United States Patent
Livnah et al.

(10) Patent No.: US 9,504,657 B2
(45) Date of Patent: Nov. 29, 2016

(54) FIXED DOSE COMBINATION THERAPY OF PARKINSON'S DISEASE

(71) Applicant: PHARMA TWO B LTD., Rehovot (IL)

(72) Inventors: Nurit Livnah, Mazkeret Batya (IL); Pninit Litman, Ness Ziona (IL); Sarit Zaksh, Modiin (IL)

(73) Assignee: PHARMATWOB LTD., Rehovot (IL)

( * ) Notice: Subject to any disclaimer, the term of this patent is extended or adjusted under 35 U.S.C. 154(b) by 0 days.

(21) Appl. No.: 14/753,801

(22) Filed: Jun. 29, 2015

(65) Prior Publication Data

US 2015/0297530 A1 Oct. 22, 2015

Related U.S. Application Data

(63) Continuation-in-part of application No. 14/372,067, filed as application No. PCT/IL2013/050025 on Jan. 10, 2013, now abandoned.

(60) Provisional application No. 61/585,824, filed on Jan. 12, 2012.

(51) Int. Cl.
| | |
|---|---|
| A61K 9/48 | (2006.01) |
| A61K 31/135 | (2006.01) |
| A61K 9/50 | (2006.01) |
| A61K 31/428 | (2006.01) |
| A61K 31/136 | (2006.01) |
| A61K 9/00 | (2006.01) |
| A61K 9/20 | (2006.01) |

(52) U.S. Cl.
CPC ........... *A61K 9/5084* (2013.01); *A61K 9/0053* (2013.01); *A61K 9/2095* (2013.01); *A61K 9/485* (2013.01); *A61K 9/4858* (2013.01); *A61K 9/4866* (2013.01); *A61K 9/501* (2013.01); *A61K 9/5015* (2013.01); *A61K 9/5031* (2013.01); *A61K 9/5047* (2013.01); *A61K 9/5089* (2013.01); *A61K 31/135* (2013.01); *A61K 31/136* (2013.01); *A61K 31/428* (2013.01)

(58) Field of Classification Search
None
See application file for complete search history.

(56) References Cited

FOREIGN PATENT DOCUMENTS

| IL | WO 2009147681 A1 * | 12/2009 | ........... A61K 31/135 |
|---|---|---|---|
| IL | WO 2011095973 A1 * | 8/2011 | ........... A61K 9/5078 |
| WO | 2006014973 A2 | 2/2006 | |
| WO | 2009147681 A1 | 12/2009 | |
| WO | 2011095973 A1 | 8/2011 | |

OTHER PUBLICATIONS

Reichmann. "Initiation of Parkinson disease treatment", Journal of Neurology 255: 57-59. (Sep. 2008) Abstract only.
Hauser et al "Advances in the pharmacologic management of early Parkinson disease". Neurologist. 13:3:126-132. (May 2007). Abstract only.
Hauser et al., "Randomized, controlled trial of rasagiline as an add-on to dopamine agonists in Parkinson's disease", Movement Disorders, pp. 1028-1034, vol. 29, No. 8 (Jun. 11, 2014).

* cited by examiner

*Primary Examiner* — Carlos Azpuru
*Assistant Examiner* — Casey Hagopian
(74) *Attorney, Agent, or Firm* — Browdy and Neimark, P.L.L.C.

(57) ABSTRACT

A pharmaceutical composition for use in treatment of Parkinson's disease is provided comprising a pharmaceutically acceptable carrier and a fixed dose combination of pramipexole and rasagiline, wherein the fixed dose combination contains a subtherapeutic dose of pramipexole and a subtherapeutic dose of rasagiline, and the dose of pramipexole is lower than or equal to the dose of rasagiline.

30 Claims, 4 Drawing Sheets

FIXED DOSE COMBINATION THERAPY OF PARKINSON'S DISEASE

CROSS-REFERENCE TO RELATED APPLICATIONS

The present application is a Continuation-in-Part of U.S. patent application Ser. No. 14/372,067, filed Jul. 14, 2014, which is a National stage of International Application No. PCT/IL2013/050025, Jan. 10, 2013, in which the United States is designated, and claims the benefit of priority from U.S. Application No. 61/585,824, filed on Jan. 12, 2012, the entire contents of each and all these applications being hereby incorporated by reference herein in their entirety as if fully disclosed herein.

FIELD OF THE INVENTION

The present invention is in the field of neurodegenerative diseases and, in particular, relates to compositions and methods for treatment of Parkinson's disease.

BACKGROUND OF THE INVENTION

Dopamine Agonists are commonly used in the treatment of Parkinson's disease; however, their use can be limited by adverse events with various levels of severity. The initiation of dopamine agonists are typically associated with nausea, vomiting and orthostatic hypotension. These side effects are more pronounced with higher doses but can usually be mitigated with a slow and complex titration schedule. Pramipexole (as well as several other DA agonists) is also associated with impulse control disorders, peripheral edema, psychosis, and sedation, that can be difficult to control and therefore limit the utility of this medication. rasagiline, another drug used in the treatment of Parkinson's disease, is largely well tolerated but also has some safety concerns particularly with respect to the risk of a cheese reaction (hypertensive crisis) with foods that are high in tyramine and a serotonin reaction (excess serotonin activity) when employed in combination with selective serotonin reuptake inhibitors and other anti-depressants that are commonly prescribed in Parkinson's disease. Among both drugs higher doses of pramipexole are typically associated with a greater risk of sever adverse effects and therefore it is important for clinicians to have treatment strategies that allow for the greatest efficacy in controlling PD symptoms, while minimizing motor complications and DA-induced adverse events.

Pharma Two B discovered that combining agents with complementary mechanisms of action (i.e., two different active agents having symptomatic or neuroprotective effects) allows for enhanced anti-Parkinsonian efficacy in comparison to what can be achieved with higher doses of either agent alone (WO2009147681). Preclinical data generated previously by Pharma Two B suggests that low doses of the MAO-B inhibitor rasagiline and the dopamine agonist pramipexole act synergistically in improving the effectiveness of these drugs. Given the relatively troublesome adverse event profile associated with initiating treatment with dopamine agonists, current treatments include a titration schedule of low doses, which are not expected to have therapeutic effect but to minimize the side effects caused by immediate start with effective doses. Moreover, undesirable effects are associated with long-term treatment with higher doses of the dopamine agonist. Thus, the option of using a combination containing low doses of dopamine agonist is favorable for many patients and may provide high therapeutic effect with minimal side effects.

SUMMARY OF INVENTION

In some aspects, the present invention provides a pharmaceutical composition for use in treatment of Parkinson's disease comprising a pharmaceutically acceptable carrier and a fixed dose combination of pramipexole and rasagiline, wherein the fixed dose combination contains a subtherapeutic dose of pramipexole and a subtherapeutic dose of rasagiline, and the dose of pramipexole is lower than or equal to the dose of rasagiline.

In another aspect, the present invention provides methods for preparing an extended release (ER) formulation of a fixed dose combination of pramipexole and rasagiline, or a pharmaceutically acceptable salt thereof, said method comprising the steps of:
(i) dissolving an active agent comprising pramipexole, rasagiline or both, optionally suitably admixed with a binder and/or a glidant, in a suitable solvent system to prepare a uniform suspension;
(ii) applying a coat of the suspension obtained in (i) to inert pellets such as inert nonpareil seeds;
(iii) optionally coating the rasagiline loaded pellets, pramipexole-loaded pellets or pellets loaded with both pramipexole and rasagiline, obtained in (ii) with an insulating/protecting sub-coating layer;
(iv) coating the pellets obtained in (ii) or (iii) with an extended-release coating layer which enables an extended release of said pramipexole and rasagiline thereby obtaining said extended release formulation;
(v) optionally blending the coated pellets obtained in (iv) with a suitable excipient; and
(vi) filling said extended release formulation into capsules or compressing said extended release formulation into tablets, wherein said capsules or tablets comprise a desired ratio of pramipexole-loaded pellets and rasagiline-loaded pellets; or said capsules or tablets comprise pellets loaded with both pramipexole and rasagiline,
thereby obtaining an extended release formulation of a fixed dose combination of pramipexole and rasagiline.

DETAILED DESCRIPTION OF THE INVENTION

Figure 1:
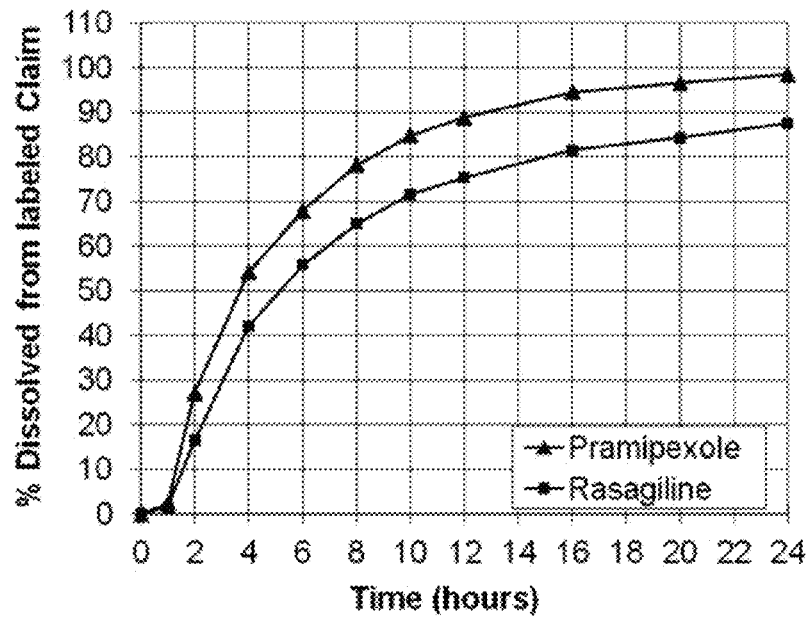
FIG. 1 shows the dissolution profile of the combination product.

The present invention is based on the finding that it is possible to use very low doses of dopamine agonist, particularly doses that are currently not typically used as monotherapy and are typically used for titration, combined with various doses of the monoamine oxidase B (MAOB) inhibitor rasagiline, and receive high efficacy, due to the synergy between the mechanisms of actions of the two drugs.

This finding enables us to decrease the doses of pramipexole and thus avoid the risk of dopamine agonist (DA)-induced adverse events, while maintaining comparable efficacy in the patients. In that way it is possible to determine more precisely the best doses of the combination of rasagiline and pramipexole that is associated with a meaningful anti-Parkinson effect and a good safety profile.

Thus, according to the present invention, a fixed dose combination containing subtherapeutic doses of pramipexole and rasagiline, or a pharmaceutically acceptable salt thereof, i.e. a dose of pramipexole that if given alone does not cause a substantial therapeutic effect and a dose of rasagiline that if given alone does not cause a substantial therapeutic effect, wherein pramipexole is present at a dose lower than or equal to the dose of rasagiline, is efficacious in treating Parkinson's disease.

The term "Fixed Dosage Combination" as used herein refers to a single dosage formulation comprising two different drugs, in this case rasagiline and pramipexole, at a precise ratio, namely, in certain fixed doses.

The term "subtherapeutic dose" as used herein refers to a dose that is below the effective monotherapy dosage levels commonly used to treat a disease, or a dose that currently is not typically used for effective monotherapy, i.e. about 1 mg/day in the case of both pramipexole and rasagiline.

In particular the molar ratio of pramipexole to rasagiline is selected from a range of 1:1 to 1:20, 1:1 to 1:10, 1:1 to 1:5, 1:1 to 1:3 or 1:1 to 1:2.

In certain embodiments, the molar ratio of pramipexole to rasagiline is selected from a range of 1:1.1 to 1:20, 1:1.1 to 1:10, 1:1.1 to 1:5, 1:1.1 to 1:3 or 1:1.1 to 1:2. In particular, this ratio is selected from a group consisting of 1:1.1, 1:1.2, 1:1.3, 1:1.4, 1:1.5, 1:1.6, 1:1.7, 1:1.8, 1:1.9, 1:2.0, 1:2.1, 1:2.2, 1:2.3, 1:2.4, 1:2.5, 1:2.6, 1:2.7, 1:2.8, 1:2.9 and 1:3.0.

In certain embodiments, the fixed dose combination contains from 0.05 mg to 1.0 mg of pramipexole and from 0.05 mg to 1.0 mg of rasagiline, provided that the dose of pramipexole is lower than or equal to the dose of rasagiline as defined above.

In certain embodiments, the fixed dose combination contains between 0.1 and 0.6 mg pramipexole and between 0.1 to 0.75 mg rasagiline.

In certain embodiments, the fixed dose combination may contain 0.05, 0.055, 0.06, 0.065, 0.07, 0.075, 0.08, 0.085, 0.09, 0.095, 0.1, 0.105, 0.11, 0.115, 0.12, 0.125, 0.13, 0.135, 0.14, 0.145, 0.15, 0.155, 0.16, 0.165, 0.17, 0.175, 0.18, 0.185, 0.19, 0.195, 0.2, 0.205, 0.21, 0.215, 0.22, 0.225, 0.23, 0.235, 0.24, 0.245, 0.25, 0.255, 0.26, 0.265, 0.27, 0.275, 0.28, 0.285, 0.29, 0.295, 0.3, 0.305, 0.31, 0.315, 0.32, 0.325, 0.33, 0.335, 0.34, 0.345, 0.35, 0.355, 0.36, 0.365, 0.37, 0.375, 0.38, 0.385, 0.39, 0.395, 0.4, 0.405, 0.41, 0.415, 0.42, 0.425, 0.43, 0.435, 0.44, 0.445, 0.45, 0.455, 0.46, 0.465, 0.47, 0.475, 0.48, 0.485, 0.49, 0.495, 0.5, 0.505, 0.51, 0.515, 0.52, 0.525, 0.53, 0.535, 0.54, 0.545, 0.55, 0.555, 0.56, 0.565, 0.57, 0.575, 0.58, 0.585, 0.59, 0.595, 0.6, 0.605, 0.61, 0.615, 0.62, 0.625, 0.63, 0.635, 0.64, 0.645, 0.65, 0.655, 0.66, 0.665, 0.67, 0.675, 0.68, 0.685, 0.69, 0.695, 0.7, 0.705, 0.71, 0.715, 0.72, 0.725, 0.73, 0.735, 0.74, 0.745, 0.75, 0.755, 0.76, 0.765, 0.77, 0.775, 0.78, 0.785, 0.79, 0.795, 0.8, 0.805, 0.81, 0.815, 0.82, 0.825, 0.83, 0.835, 0.84, 0.845, 0.85, 0.855, 0.86, 0.865, 0.87, 0.875, 0.88, 0.885, 0.89, 0.895, 0.9, 0.905, 0.91, 0.915, 0.92, 0.925, 0.93, 0.935, 0.94, 0.945, 0.95, 0.955, 0.96, 0.965, 0.97, 0.975, 0.98, 0.985, 0.99, 0.995 or 1 mg of pramipexole; and 0.05, 0.055, 0.06, 0.065, 0.07, 0.075, 0.08, 0.085, 0.09, 0.095, 0.1, 0.105, 0.11, 0.115, 0.12, 0.125, 0.13, 0.135, 0.14, 0.145, 0.15, 0.155, 0.16, 0.165, 0.17, 0.175, 0.18, 0.185, 0.19, 0.195, 0.2, 0.205, 0.21, 0.215, 0.22, 0.225, 0.23, 0.235, 0.24, 0.245, 0.25, 0.255, 0.26, 0.265, 0.27, 0.275, 0.28, 0.285, 0.29, 0.295, 0.3, 0.305, 0.31, 0.315, 0.32, 0.325, 0.33, 0.335, 0.34, 0.345, 0.35, 0.355, 0.36, 0.365, 0.37, 0.375, 0.38, 0.385, 0.39, 0.395, 0.4, 0.405, 0.41, 0.415, 0.42, 0.425, 0.43, 0.435, 0.44, 0.445, 0.45, 0.455, 0.46, 0.465, 0.47, 0.475, 0.48, 0.485, 0.49, 0.495, 0.5, 0.505, 0.51, 0.515, 0.52, 0.525, 0.53, 0.535, 0.54, 0.545, 0.55, 0.555, 0.56, 0.565, 0.57, 0.575, 0.58, 0.585, 0.59, 0.595, 0.6, 0.605, 0.61, 0.615, 0.62, 0.625, 0.63, 0.635, 0.64, 0.645, 0.65, 0.655, 0.66, 0.665, 0.67, 0.675, 0.68, 0.685, 0.69, 0.695, 0.7, 0.705, 0.71, 0.715, 0.72, 0.725, 0.73, 0.735, 0.74, 0.745, 0.75, 0.755, 0.76, 0.765, 0.77, 0.775, 0.78, 0.785, 0.79, 0.795, 0.8, 0.805, 0.81, 0.815, 0.82, 0.825, 0.83, 0.835, 0.84, 0.845, 0.85, 0.855, 0.86, 0.865, 0.87, 0.875, 0.88, 0.885, 0.89, 0.895, 0.9, 0.905, 0.91, 0.915, 0.92, 0.925, 0.93, 0.935, 0.94, 0.945, 0.95, 0.955, 0.96, 0.965, 0.97, 0.975, 0.98, 0.985, 0.99, 0.995, or 1 mg of rasagiline, provided that the dose of pramipexole is lower than or equal to the dose of rasagiline as defined above.

A clinical trial conducted by the Applicant in accordance with the present invention has demonstrated for the first time that a fixed dose combination (FDC) of low dosages of rasagiline (0.75 mg) with two pramipexole doses (0.3 mg or 0.6 mg, doses that were previously used only for titration) in a controlled release oral formulation, provide a highly significant positive clinical effect in early stage Parkinson's disease (PD) patients, when compared to placebo. Both dosages of the FDC, in a dose dependent manner, were found to be significantly active in improvement of the symptoms of PD, in early stage patients in all assessments done in this study including Unified Parkinson's Disease Rating Scale (UPDRS) total score and sub scales, Parkinson Disease Questionnaire 39 (PDQ39) and total UPDRS responder analysis. Moreover, both dosages of FDC are well tolerated and the profile of the adverse affects (AEs) is favorable, particularly in the FDC-B 0.3/0.75 treatment group, in particular in comparison with the known AEs of current pramipexole treatment regiments.

The clinical trial results strongly support the observations from the preclinical studies and the scientific hypothesis of the product development, claiming that the strong synergy between rasagiline and pramipexoel, enhanced by the adapted sustained release profile allowing the drugs to act together for a longer time, lead to a high clinical effect of the combination, which was never before shown in the low doses used in the FDC.

Thus, in certain embodiments, the fixed dose combination may contain 0.3 mg or 0.6 mg pramipexole and 0.75 mg rasagiline, i.e. 0.3 mg pramipexole and 0.75 mg rasagiline or 0.6 mg pramipexole and 0.75 mg rasagiline. The pharmaceutical composition may be formulated for extended release and/or for oral administration as explained below.

For purposes of clarity, and in no way limiting the scope of the teachings, unless otherwise indicated, all numbers expressing quantities, percentages or proportions, and other numerical values recited herein, should be interpreted as being preceded in all instances by the term "about." Accordingly, the numerical parameters recited in the present specification are approximations that may vary depending on the desired outcome. For example, each numerical parameter may be construed in light of the number of reported significant digits and by applying ordinary rounding techniques.

Any dose range, amount range, concentration range, percentage range, or ratio range recited herein are to be understood to include doses, concentrations, percentages or ratios of any integer within that range, and up to one tenths of the upper or lower limit beyond that range, and fractions thereof, such as one tenth and one hundredth of an integer, unless otherwise indicated.

In other embodiments, the pramipexole and rasagiline are formulated for extended release (ER). The term "extended release" is used herein interchangeably with the terms "prolonged-action", "repeat-action", "controlled release", and "sustained-release" and refers to the release of an active agent at predetermined intervals or gradually, in such a manner as to make the contained active agent available over an extended period of time following ingestion.

In certain embodiments, all or nearly all pramipexole and rasagiline in the fixed dose combination is gradually released from the extended release formulation over a period of 24 hours.

The pharmaceutical composition may be in the form of a monolithic matrix; a tablet, preferably a bi- or multi-layered tablet, matrix tablet, disintegrating tablet, dissolving tablet, or chewable tablet; a capsule or sachet, preferably filled with granules, grains, beads, or pellets; or a depot system based on a biodegradable polymer such as poly(D,L-lactide) (PLA), polyglycolide (PGA), and poly(D,L-lactide-co-glycolide) (PLGA), and it may be formulated for oral administration.

The active agent may be suitably admixed with a binder and/or a glidant, in a suitable solvent system to prepare a uniform suspension and then applied to inert pellets to form a thin coat. In the case of the present invention, rasagiline and pramipexole may be dissolved in separate solvents and sprayed separately on different pellets to form rasagiline loaded pellets and pramipexole-loaded pellets; or each separate solution may be sprayed on the same pellets to form pellets loaded with both rasagiline and pramipexole. Alternatively, rasagiline and pramipexole may be dissolved in a common solvent to form a common uniform solution, or the separate solutions may be mixed to form a common uniform solution, and the common uniform solution may be sprayed on pellets to form pellets loaded with both rasagiline and pramipexole.

In the next step, which is optional, the rasagiline loaded pellets, the pramipexole-loaded pellets or the pellets loaded with both rasagiline and pramipexole, are coated with an insulating/protecting sub-coating layer, after which the pellets are coated with an extended-release coating layer which enables an extended release of the rasagiline and pramipexole thereby obtaining said extended release formulation. The coated pellets may then be blended with a suitable excipient, and finally the extended release formulation is filled into capsules or compressed into tablets, wherein said capsules or tables comprise a desired ratio of rasagiline loaded pellets and pramipexole-loaded pellets; or said capsules or tablets comprise pellets loaded with both rasagiline and pramipexole.

The desired ratio, as defined herein above, may be obtained using any method that will provide the desired result, such as, but not limited to, weighing, measuring the volume of, or counting, the rasagiline loaded pellets and pramipexole-loaded pellets separately and filling the capsule, or compressing the tablet, with the desired weight, volume or number of each active agent-loaded pellet. Preferably, the pellets are weighed separately and filled at the desired ratio into capsules or pressed into tablets, or mixed together at a pre-determined ratio and the mix is weighed into the capsule. In the case of pellets loaded with both rasagiline and pramipexole, the ratio is determined at the stage of coating the inert pellets, in which a solution with the desired ratio of the two agents is spayed on the inert pellets, or two separate solutions are sprayed in layers on the inert pellets, at the desired ratio.

Thus, in certain embodiments, pharmaceutical composition of the present invention comprises extended-release pellets comprising (i) an inert pellet core; (ii) a drug layer coating said pellet core, said drug layer comprising an active agent comprising rasagiline, pramipexole or both, or a pharmaceutically acceptable salt thereof, optionally suitably admixed with a binder and/or a film-former polymer, and further optionally admixed with a glidant; (iii) optionally an isolating/protecting sub-coating layer coating said drug layer; and (iv) an extended-release coating layer coating said sub-coating layer, if present, or said drug layer.

The ER pellet of the present invention may optionally comprise an isolating/protecting sub-coating layer coating said drug layer. The role of this sub-coating layer is to isolate the active material layer from the external ER coating and protect from possible interactions with the active agent that might affect its stability and lead to formation of active pharmaceutical ingredient (API) degradation products. In certain embodiments, the sub-coating layer comprises a film-former polymer and optionally a glidant.

The ER pellet of the present invention comprises an outer ER coating layer, also termed herein "a functional layer", coating either the sub-coating layer, if present, or the drug layer.

In certain embodiments, the ER coating layer comprises at least one pH-independent polymer, i.e., a water swelling/water insoluble/hydrophobic polymer, and optionally a pore-forming agent, wherein the extended-release pellet has a pH-independent in vitro release characteristic. In other embodiments, the functional layer comprises a pH-independent polymer, a hydrophilic release modulator polymer acting as a pore-forming agent, and optionally a hydrophobic or hydrophilic plasticizer, and/or glidant. In further certain embodiments, the ER coating layer comprises a mixture of a pH-dependent enteric-coating polymer and a pH-independent polymer, wherein the extended-release pellet has a close to zero order in vitro release characteristic at either acidic or physiological pH, i.e., at pH values of up to 7.4.

Binders for pharmaceutical use are hydrophilic substances, such as sugars and polymers of natural and synthetic origin, used in the manufacture of solid dosage forms due to their adhesive and cohesive properties. The role of binders is to assist size enlargement by adding cohesiveness to powders, thereby providing granules and tablets with the necessary bonding strength. Although binders improve the appearance, hardness and friability of these preparations, they are not intended to influence the disintegration or dissolution rates of the active substances. Binders of natural origin, which have been commonly used in the past, include acacia, gelatin, starch, and hydrolyzed starch. Those substances have been replaced by binders of synthetic origin, the most important of which are povidone and various cellulose derivatives. Examples of binders that can be admixed with the active agent in the drug layer coating of the ER pellet of the invention include, without being limited to, a polyvinyl pyrrolidone (PVP), hydroxypropylmethyl cellulose (HPMC), hydroxypropyl cellulose (HPC), microcrystalline cellulose, and combinations thereof. The binder may be present in an amount from 0.5% to 20%, preferably from 0.5% to 10%, by weight of the entire pellet.

The term "film-former polymer" as used herein refers to polymers capable of hardening to coherent films. In addition, the physical property of these polymers that is essential for coating is the ability to form films or certain adhesiveness to the material to be coated. Examples of film-former polymers include, without limiting, PVP, HPMC, HPC, microcrystalline cellulose, and combinations thereof. The film-former polymer when comprised within the drug layer may be present in an amount of up to 90% by weight of the entire drug layer, preferably from 0.5% to 20%, by weight of the entire pellet. The amount of film-former polymer in the sub-coating layer may be up to 100% by weight of the entire sub-coating layer, preferably from 0.5% to 10%, by weight of the entire pellet.

Glidants are typically added to pharmaceutical compositions to enhance flowability of granulations and powders by reducing friction and surface charge. In addition, they are used as anti-tack a gents during the coating process. Particular glidants such as talc and glyceryl monostearate are commonly used in coating formulations as anti-tack agents, which reduce the sticking tendency at lower product temperatures. Other glidants such as silicon dioxide colloidal provide desirable flow characteristics that are exploited to improve the flow properties of dry powders in a number of processes such as tableting and capsulation, due to their small particle size and large specific surface area. Non-limiting examples of glidants include talc, particularly talc extra fine, colloidal silicon dioxide, glyceryl monostearate, and combinations thereof.

The glidants, when comprised within the drug layer, may be present in an amount of up to 30% by weight of the entire drug layer, preferably from 0.5% to 5%, by weight of the entire pellet. The amount of glidant when comprised within the sub-coating layer may be up to 10% by weight of the entire sub-coating layer, preferably from 0.5% to 5%, by weight of the entire pellet.

Examples of pH-independent polymers that may be comprised within the ER pellet of the invention include, without being limited to, ethyl cellulose, Surelease®, copolymers of acrylic and methacrylic acid esters such as Eudragit® RL (poly(ethylacrylate, methylmethacrylate, trimethylammonioethyl methacrylate chloride), 1:2:0.2), Eudragit® RS (poly(ethylacrylate, methyl methacrylate, trimethylammonioethyl methacrylate chloride), 1:2:0.1), Eudragit® NE (poly(ethylacrylate, methylmethacrylate), 2:1), and combinations thereof. The pH-independent polymer may be present in an amount from 10% to 50%, preferably from 10% to 30%, by weight of the entire pellet.

Examples of pH-dependent enteric-coating polymers that may be comprised within the ER pellet of the invention include, without limiting, Eudragit® S (poly(methacrylicacid, methylmethacrylate), 1:2), Eudragit® L 55 (poly (methacrylicacid, ethylacrylate), 1:1), Kollicoat® (poly (methacrylicacid, ethylacrylate), 1:1), hydroxypropyl methylcellulose phthalate (HPMCP), alginates, carboxymethylcellulose, and combinations thereof. The pH-dependent enteric-coating polymer may be present in an amount from 10% to 50%, preferably from 10% to 30%, by weight of the entire pellet.

The term "pore-forming agent" as used herein refers to a substance that dissolves in the body environment, thus forming open pores in the matrix that increase the diffusion rate of the active agent through the coating layer. The size of the pores formed can, to some extent, be controlled by the size of the solid particulate material being used. For uniformity of pores, the particulate material can be screened through successively finer mesh sieves to produce a desired range of particle sizes. The pore-forming agent that may be comprised within the ER pellets of the invention is either inorganic or organic substance, including, e.g., polyvinylpyrrolidone (PVP), polyethylene glycol (PEG), HPMC, HPC, methylcellulose, 1,2-propylene glycol, lactose, sucrose, talc, particularly talc extra fine, and combinations thereof. The pore-forming agent may be present in an amount from 0.1% to 20%, preferably from 0.1% to 10%, by weight of the entire pellet.

The term "hydrophilic release modulator polymer" as used herein refers to a polymer that is water soluble and controls the release of the active agent. Nevertheless, in certain embodiments, the hydrophilic release modulator polymer comprised within the ER coating layer of the ER pellet of the invention acts, in fact, as a pore-forming agent. Examples of hydrophilic release modulator polymers include, without being limited to, PVP, PEG, HPMC, HPC, and combinations thereof. The hydrophilic release modulator polymer may be present in an amount from 0.1% to 20%, preferably from 0.1% to 10%, by weight of the entire pellet.

The term "plasticizer" as used herein includes any compound or combination of compounds capable of plasticizing or softening a polymer used in the ER pellet of the present invention. During manufacture of the ER coating layer, the plasticizer can lower the melting temperature or glass transition temperature (softening point temperature) of the polymer or combination of polymers used; can broaden the average molecular weight of said polymer or combination of polymers, and can further reduce the viscosity of said polymer or combination of polymers for convenient processing of the coat solution. Non-limiting examples of plasticizers include dibutyl sebacate; dibutyl phthalate; citrate esters, such as triethylcitrate, and triacetin; propylene glycol; low molecular weight poly(alkylene oxides), such as PEG, poly(propylene glycols), and poly(ethylene/propylene glycols); and combinations thereof. The plasticizers may be present in an amount from 0.1% to 20%, preferably from 0.1% to 10%, by weight of the entire pellet.

The ER pellet of the present invention may comprise further inactive ingredients such as osmotic pressure/tonicity agent. Such agents are commonly used for time-controlled disintegration when a pulsatile drug delivery is required. Examples of suitable osmotic/tonicity excipients that may be used in the preparation of the ER pellet include, without being limited to, sodium chloride and mannitol. The osmotic/tonicity agent when comprised in the ER pellet may be present in an amount of up to 20%, preferably from 0.5% to 10%, by weight of the entire pellet.

In particular embodiment exemplified herein, the ER pellets exemplified herein comprises an inert pellet core; a drug layer comprising the active agent admixed with PVP as a film-former polymer/binder and with talc extra fine as a glidant; and an ER coating layer comprising ethylcellulose as a pH-independent polymer, and PEG as a pore-forming agent, wherein the amount of said film-former polymer/binder is up to 90% by weight of the entire drug layer, or from 0.5% to 20% by weight of the entire pellet; the amount of said glidant is up to 30% by weight of the entire drug layer, or from 0.1% to 10% by weight of the entire pellet; the amount of said pH-independent polymer is from 50% to 90% by weight of the entire ER coating layer, or from 10% to 30% by weight of the entire pellet; and the amount of said pore-forming agent is from 1% to 20% by weight of the entire ER coating layer, or from 0.1% to 10% by weight of the entire pellet.

In other particular embodiments exemplified herein, the ER pellet of the present invention comprises an inert pellet core; a drug layer comprising said active agent admixed with PVP as a film-former polymer/binder and with talc extra fine as a glidant; an isolating/protecting sub-coating layer comprising PVP as a film-former polymer; and an ER coating layer comprising ethylcellulose as a pH-independent polymer, PEG as a pore-forming agent, and talc extra fine as a glidant, wherein the amount of said film-former polymer/binder in said drug layer is up to 90% by weight of the entire drug layer, or from 0.5% to 20% by weight of the entire pellet; the amount of said glidant in said drug layer is up to 30% by weight of the entire drug layer, or from 0.1% to 10% by weight of the entire pellet; the amount of said film-former polymer in said sub-coating layer is up to 100% by weight of the entire sub-coating layer, or from 0.5% to 20% by weight of the entire pellet; the amount of said pH-independent polymer is from 50% to 90% by weight of the entire ER coating layer, or from 10% to 30% by weight of the entire pellet; the amount of said pore-forming agent is from 1% to 20% by weight of the entire ER coating layer, or from 0.1% to 10% by weight of the entire pellet; and the amount of said glidant in said ER coating layer is from 0.1% to 20% by weight of the entire ER coating layer, or from 0.1% to 10%, by weight of the entire pellet.

In certain embodiments, the extended-release pellets are blended with one or more suitable excipients and either filled into a capsule or compressed into a tablet, wherein said capsule or tablet comprises extended-release pellets comprising extended-release pellets comprising rasagiline and extended-release pellets comprising pramipexole, or extended-release pellets comprising both rasagiline and pramipexole.

The preparation of such capsules or tablets may be carried out using any suitable technology known in the art.

Examples of suitable excipients, which may be used in the preparation of the oral pharmaceutical composition include, without being limited to, silicon dioxides, as well as other glidants known in the art as defined above.

Tablets fillers fill out the size of a tablet or capsule, making it practical to produce and convenient for the consumer to use. By increasing the bulk volume, the fillers make it possible for the final product to have the proper volume for patient handling. A good filler must be inert, compatible with the other components of the formulation, non-hygroscopic, relatively cheap, compactible, and preferably tasteless or pleasant tasting. Plant cellulose (pure plant filler) is a popular filler in tablets or hard gelatin capsules. Dibasic calcium phosphate is another popular tablet filler. A range of vegetable fats and oils can be used in soft gelatin capsules. Tablet fillers include, e.g., lactose, mannitol/Parteck®, sorbitol, starch, and combinations thereof.

Disintegrant expand and dissolve when wet causing the tablet to break apart in the digestive tract, releasing the active ingredients for absorption. Disintegrant types include water uptake facilitators and tablet rupture promoters. They ensure that when the tablet is in contact with water, it rapidly breaks down into smaller fragments, facilitating dissolution. Non-limiting examples of disintegrants include crosslinked polyvinylpyrrolidone (crospovidone), sodium/calcium carboxymethyl cellulose (CMC), croscarmellose sodium hydroxypropyl cellulose low-substituted, sodium bicarbonate, starch, sodium starch glycolate, and combinations thereof.

Lubricants are added in small quantities to tablet and capsule formulations to improve certain processing characteristics. More particular, these agents prevent ingredients from clumping together and from sticking to the tablet punches or capsule-filling machine. Lubricants also ensure that tablet formation and ejection can occur with low friction between the solid and die wall. Examples of lubricants include, without limiting, glyceryl behenate, stearic acid, talc, zinc stearate, calcium stearate, and combinations thereof.

In another aspect, the present invention relates to a method for treatment of Parkinson's disease, comprising administering to a patient in need a therapeutically effective amount of a pharmaceutical composition for use in treatment of Parkinson's disease comprising a pharmaceutically acceptable carrier and a fixed dose combination of pramipexole and rasagiline, wherein the fixed dose combination contains a subtherapeutic dose of pramipexole and a subtherapeutic dose of rasagiline, and the dose of pramipexole is lower than or equal to the dose of rasagiline.

The terms "treat", "treatment" and "provide substantial therapeutic effect" are used interchangeably herein and refer to stopping, slowing down, reducing the extent of or minimizing the neurodegenerative process in nigrostriatal neurons (neuroprotective therapy), eliminating or reducing the biochemical imbalance, increasing dopamine synthesis, stimulating dopamine receptors activity and dopamine release from the presynaptic space, and/or inhibiting dopamine reuptake by presynaptic receptors and dopamine catabolism. The terms may also refer to improving or slowing worsening of symptoms of Parkinson's disease such as tremor, slowed motion (bradykinesia), Restless Leg Syndrome, rigid muscles, impaired posture and balance, loss of automatic movements, speech changes, impaired sleep and/or impaired quality of life (QOL), eliminating or reducing physical, cognitive or mental symptoms of Parkinson's disease and even possibly slowing down or arresting the progress of dementia.

Improvement, reduction or slowing of worsening of symptoms of Parkinson's disease may be measured by assessing one or more accepted parameters before and during the term of the treatment, such as, but not limited to, the Unified Parkinson's Disease Rating Scale (UPDRS) score, UPDRS activity of daily life (ADL) and motor sub-scores, Beck Depression Inventory®-II (BDI-II), International Restless Leg Syndrome Rating Scale (IRLS) symptoms, Parkinson Disease Questionnaire 39 (PDQ39), Clinical Global Impression (CGI).

In still other aspects, the present invention relates to a fixed-dose-combination as defined herein above, for use in the treatment of Parkinson's disease; or for the preparation of a medicament for the treatment of Parkinson's disease.

In yet another aspect, the present invention provides a method for preparing an extended release formulation of a fixed dose combination of pramipexole and rasagiline, or a pharmaceutically acceptable salt thereof, said method comprising the steps of: (i) dissolving an active agent comprising pramipexole, rasagiline or both, optionally suitably admixed with a binder and/or a glidant, in a suitable solvent system to prepare a uniform suspension; (ii) applying a coat of the suspension obtained in (i) to inert pellets such as inert nonpareil seeds; (iii) optionally coating the rasagiline loaded pellets, pramipexole-loaded pellets or pellets loaded with both rasagiline and pramipexole obtained in (ii) with an insulating/protecting sub-coating layer; (iv) coating the pellets obtained in (ii) or (iii) with an extended-release coating layer which enables an extended release of said rasagiline and pramipexole thereby obtaining said extended release formulation; (v) optionally blending the coated pellets obtained in (iv) with a suitable excipient; and (vi) filling said extended release formulation into capsules or compressing said extended release formulation into tablets, wherein said capsules or tables comprise a ratio of rasagiline loaded pellets and pramipexole-loaded pellets selected from a range of 1:1.1 to 1:20, 1:1.1 to 1:10, 1:1.1 to 1:5, 1:1.1 to 1:3 or 1:1.1 to 1:2; or said capsules or tablets comprise pellets loaded with both rasagiline and pramipexole at a ratio selected from a range of 1:1.1 to 1:20, 1:1.1 to 1:10, 1:1.1 to 1:5, 1:1.1 to 1:3 or 1:1.1 to 1:2, thereby obtaining an extended release formulation of a fixed dose combination of rasagiline and pramipexole.

The invention will now be illustrated by the following non-limiting examples.

EXAMPLES

Example 1

Formulation and Dissolution Profile of the Combination Product

Each component was formulated separately (Tables 1 and 2) and the beads were encapsulated in respective weights to give a dose of 0.6 mg pramipexole and 0.75 mg rasagiline.

Analytical Method—Dissolution Test for the Combination Product

The method evaluates the dissolution profile for the active pharmaceutical ingredients (API's) pramipexole (PPX) and rasagiline (RAS) in coated pellets formulated for extended release (ER), packed in capsule, by using high performance liquid chromatography (HPLC) for quantitative analysis.

The content of one capsule or one dose of beads (pellets) sample, was placed into a basket, which rotates inside a vessel containing a medium, under constant specified rate and temperature. Sample was dissolved in the medium solution over time in a rate that reflected the release profile of the formulation, thus the solution contains different concentrations of API's at different time points. Samples were taken automatically or manually at specified time points within specified time interval, filtered through 20 μm PE, Cat. No 400111, Sun Sri filter and quantified against reference standards solutions.

TABLE 1

| Rasagiline mesylate ER coated pellets with sub coating | |
|---|---|
| Ingredients | Mg/capsule (22% ER) |
| Cores - drug layered coated pellets | |
| Ethanol 96% | — |
| Distilled water | — |
| rasagiline mesylate | 1.17 |
| PVP K25 | 6.27 |
| Talc extra fine | 0.78 |
| Sugar spheres 600-710 μm | 70.20 |
| Total core weight | 78.42 |
| Cores - sub coated pellets | |
| Distilled water | — |
| Ethanol 96% | — |
| PVP K25 | 2.36 |
| Total SC core weight | 80.78 |
| Functional coating (ER coating) | |
| Acetone | — |
| Ethanol 96% | — |
| Distilled water | — |
| Ethocel 45 cps | 15.99 |

TABLE 1-continued

| Rasagiline mesylate ER coated pellets with sub coating | |
|---|---|
| Ingredients | Mg/capsule (22% ER) |
| PEG 3000 | 0.89 |
| Talc extra fine | 0.89 |
| Total ER pellets weight | 98.55 |
| Dry mix | |
| Silicon dioxide colloidal | 0.09 |
| Total | 98.64 |

TABLE 2

| Pramipexole Dihydrochloride Monohydrate ER coated pellets with sub | |
|---|---|
| Ingredients | Mg/capsule (18% ER) |
| Cores - drug layered coated pellets | |
| Ethanol 96% | — |
| Distilled water | — |
| pramipexole Dihydrochloride Monohydrate | 0.60 |
| PVP K25 | 16.54 |
| Talc extra fine | 1.90 |
| Sugar spheres 600-710 μm | 104.76 |
| Total core weight | 123.80 |
| Cores - sub coated pellets | |
| Distilled water | — |
| Ethanol 96% | — |
| PVP K25 | 3.71 |
| Total SC core weight | 127.51 |
| Functional coating (ER coating) | |
| Acetone | — |
| Ethanol 96% | — |
| Distilled water | — |
| Ethocel 45 cps | 20.65 |
| PEG 3000 | 1.15 |
| Talc extra fine | 1.15 |
| Total ER pellets weight | 150.46 |
| Dry mix | |
| Silicon dioxide colloidal | 0.14 |
| Total | 150.60 |

The conditions used for the experiment disclosed in Table 3 were:
Apparatus: 1 (baskets)
Medium: Intestinal Fluid Simulated (IFS), a buffer that mimics intestinal conditions
Speed: 100 rpm
Temperature: 37° C.±0.5° C.

The amount of RAS and PPX dissolved was determined using HPLC.

Results of Analytical Method—Dissolution Test for the Combination Product Capsule.

TABLE 3

Dissolution profile of the combination product capsule (see FIG. 1 for graphical representation)

| Time (hrs) | Rasagiline mesylate % Dissolved | Pramipexole Dihydrochloride Monohydrate % Dissolved |
|---|---|---|
| 0 | 0 | 0 |
| 1 | 1.5 | 2.3 |
| 2 | 16.5 | 27.1 |
| 4 | 42.0 | 54.1 |
| 6 | 55.8 | 68.0 |
| 8 | 65.1 | 78.3 |
| 10 | 71.7 | 84.9 |
| 12 | 75.5 | 88.8 |
| 16 | 81.5 | 94.6 |
| 20 | 84.4 | 96.6 |
| 24 | 87.6 | 98.5 |

Example 2

In Vivo Study of Drugs in MPTP Model of Parkinson's Disease

Material and Methods
Models.

Experimental models of Parkinson's disease (PD) are needed to gain insights into the possible pathological mechanisms of the disease. In addition to this function, they are essential in the development and testing of new therapeutic strategies, whether pharmacological or otherwise.

MPTP Mice Model.

A significant body of biochemical data from human brain autopsy studies and those from animal models point to an ongoing process of oxidative stress in the substantia nigra which could initiate dopaminergic neurodegeneration. It is not known whether oxidative stress is a primary or secondary event. Nevertheless, oxidative stress, as induced by the neurotoxin MPTP (N-methyl-4-phenyl-1,2,3,6-tetrahydropyridine), has been used in animal models to investigate the process of neurodegeneration with the intent to develop antioxidant neuroprotective drugs.

TABLE 4

Groups allocation

| Group (6-10 mice each group) | Treatments (Daily) |
|---|---|
| 1M | Naive Saline + Saline |
| 2M | 40 mg/kg MPTP-HCL + saline |
| 3M | 40 mg/kg MPTP-HCL + rasagiline dose 0.15 mg/Kg |
| 4M | 40 mg/kg MPTP-HCL + pramipexole dose 0.12 mg/Kg |
| 5M | 40 mg/kg MPTP-HCL + pramipexole dose 0.1 mg/Kg |
| 6M | 40 mg/kg MPTP-HCL + pramipexole dose 0.075 mg/Kg |
| 7M | 40 mg/kg MPTP-HCL + rasagiline dose 0.15 mg/Kg + pramipexole dose 0.12 mg/Kg |
| 8M | 40 mg/kg MPTP-HCL + rasagiline dose 0.15 mg/Kg + pramipexole dose 0.1 mg/Kg p |
| 9M | 40 mg/kg MPTP-HCL + rasagiline dose 0.15 mg/Kg + pramipexole dose 0.075 mg/Kg p |

The neurotoxin MPTP is converted in the brain into the positively charged molecule MPP+(1-methyl-4-phenylpyridinium) by the enzyme MAO-B, causing parkinsonism in primates by killing certain dopamine-producing neurons in the substantia nigra. It acts by interfering with oxidative phosphorylation in mitochondria, causing depletion of ATP and cell death. It also inhibits the synthesis of catecholamines, reduces levels of dopamine and cardiac norepinephrine, and inactivates tyrosine hydroxylase.

Experimental Procedure:

Male C57Bl/6 mice weighing 20+/−1 g are used (6-10 mice per group). MPTP is administrated by intraperitonealy (IP) injection at a dose of 40 mg/Kg per day for 5 days. Controls are naïve untreated mice injected with saline, and MPTP treated mice injected with saline (no drug treatment). Drugs, rasagiline (0.15 mg/Kg) and pramipexole (3 different doses of 0.12, 0.1 and 0.075 mg/Kg), are given alone or in 3 fixed dose combinations of rasagiline and pramipexole. The fixed dose combinations are composed of rasagiline at a constant dose of 0.15 mg/Kg and pramipexole at 3 different doses as indicated above. Both drugs are dissolved together at saline from their stock solutions to give the final desired combination dose. The application of the drugs is done daily intraperitonealy (IP) injection 30 minutes before MPTP administration. Drug treatment is prolonged for 12 days. The effect of the treatments is assessed by measurement of dopamine and its metabolites (dihydroxyphenylacetic acid and Homovanillic acid) in left and right striatum together taken from the mice at the end of the experiment.

The study included 9 groups of 6-10 mice each. The mice are treated with MPTP to induce the Parkinson model, and treated with combinations with constant dose of rasagiline and varying doses of pramipexole. Controls are naïve untreated mice injected with saline, and MPTP treated mice injected with saline (no drug treatment). The groups are treated according to the Table 4 above. The testing schedule is shown in Table 5.

TABLE 5

Testing Time Table - First Dosing Day 0

| Test | Dosing (Test Compounds) |
|---|---|
| Study | Dosing (MPTP) |

| Days | 0 | 1 | 2 | 3 | 4 | 5 | 6 | 7 | 8 | 9 | 10 | 11 | 12 |
|---|---|---|---|---|---|---|---|---|---|---|---|---|---|
| MPTP | ✓ | ✓ | ✓ | ✓ | ✓ | | | | | | | | End of Study |
| Test items | ✓ | ✓ | ✓ | ✓ | ✓ | ✓ | ✓ | ✓ | ✓ | ✓ | ✓ | ✓ | |

Sample Preparation for HPLC Analysis of Dopamine and Metabolites.

Striatum tissue samples are homogenized in ice in 500 µl homogenization buffer (0.1M perchloric acid, 0.02% EDTA and 1% ETOH) using OMNI Tip homogenizing kit of OMNI International (intermediate speed, 3×10 seconds with 5 seconds intervals). The homogenates are sonicated for 5 minutes then centrifuged at 15,000 RPM at 4° C. for 15 min. The supernatants are transferred into fresh tubes and Dopamine content is analyzed by HPLC.

Figure 2:
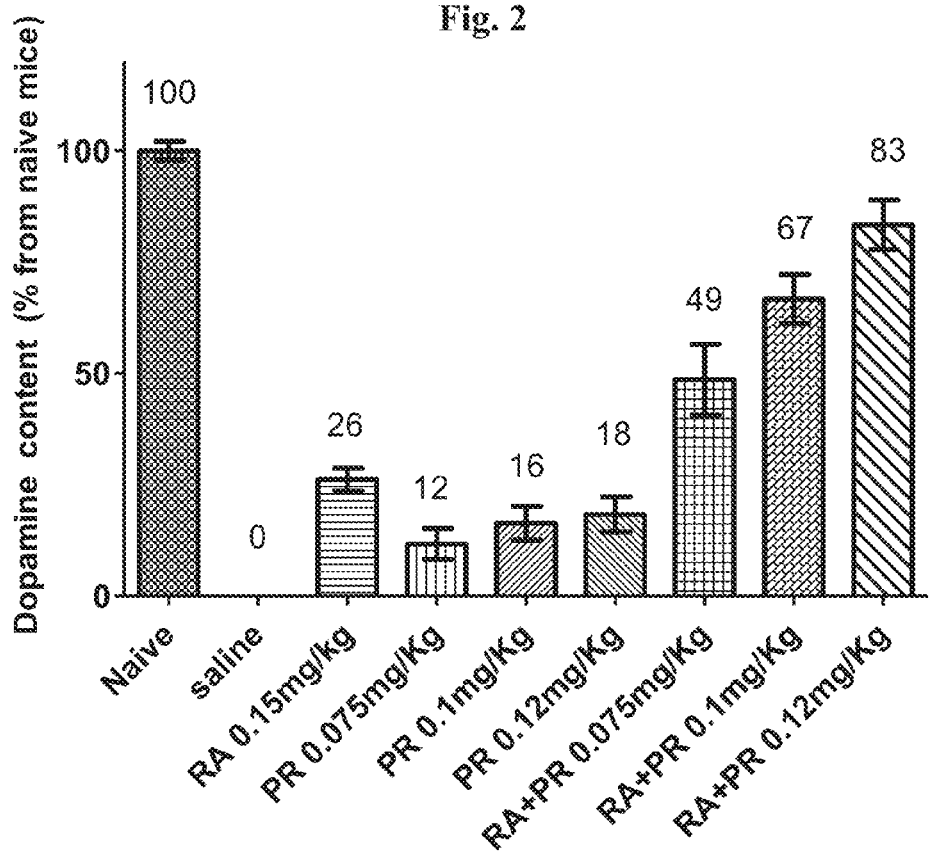
FIG. 2 shows dose dependent synergistic effect of pramipexole, rasagiline and their combination, on dopamine levels in mouse brain.

The results of this experiment are presented in FIG. 2. Dopamine levels in naive mice brain were normalized to 100%, while Dopamine levels of MPTP-PD-mice treated with saline were normalized to 0%. The graph reflects effect of the different treatments on Dopamine levels compared to saline. It is clearly seen that the FDC is highly synergistic, where the effect of rasagiline and all three doses of pramipexole when given as monotherapies, is very low, while the combination containing the same doses is highly effective, and notably, remarkably more effective than the sum of the effect of both components. The effect of the combination is dose dependent, with efficacy increasing in correlation with the increase in pramipexole dose, however, the dose response is remarkably more significant than the dose-response in the effect of the increasing doses of Pramipexole when given alone. This implies that the addition of Rasagiline is much more than a simple additive effect and suggest a strong synergistic effect of the combination in the reported conditions.

Thus, the mice study shows clearly, that when the drugs in the combination product of the present invention are administered as fixed dose combination, in doses that have very low or no effect as monotherapies, they give a therapeutic effect that is larger than the sum of their individual effects, indicating that this synergistic effect, probably arising from their complementary biological mechanisms. This suggests that if we employ, in a human trial, doses that are subtherapeutic, or lower than the ones currently employed as effective monotherapies, we will also see a significant effect, as can be anticipated by the results in the mice study.

Example 3

Phase I Pharmacokinetic Study in Healthy Volunteers

Pharma Two B conducted a 4 arms crossover study in healthy fasted volunteer adults comparing a single dose marketed immediate release rasagiline (Azilect, 1 mg), marketed extended release pramipexole (Mirapex ER, 0.75 mg), both marketed drugs taken together, and Pharma Two B's proprietary extended-release combination product containing doses of rasagiline (1 mg) and pramipexole (0.75 mg) that equal to the commercially available mono-therapy products.

Co-Administration of Monotherapies.

Evaluation of the plasma concentrations of pramipexole showed no statistically significant effect of concomitant rasagiline administration on pramipexole pharmacokinetics. Co-administration of Mirapex ER and Azilect resulted in only a 4% decrease in pramipexole $C_{max}$ and a 3% increase in $AUC_{inf}$. Similarly, no statistically significant effect of concomitant pramipexole administration was observed on rasagiline pharmacokinetics. Rasagiline $C_{max}$ and $AUC_{inf}$ increased 3% and 4% respectively when co-administered with Mirapex ER (Table 6).

Co-Administration of Monotherapies Versus the Combination Product.

Figure 3A:
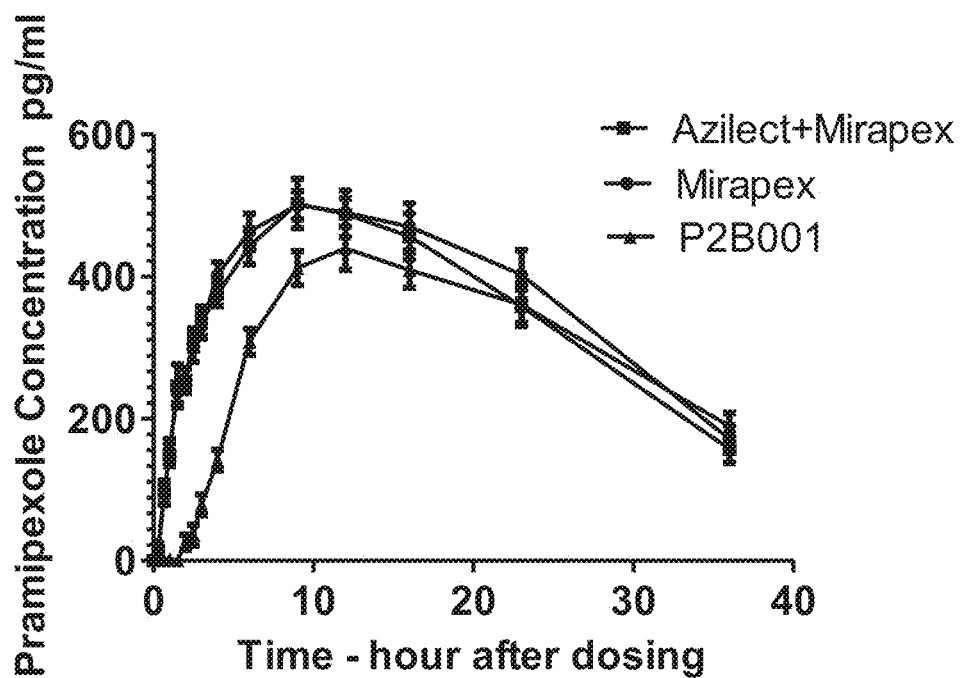
FIGS. 3A-B depict a pharmacokinetic study of FDC (FDC containing 1 mg rasagiline and 0.75 mg pramipexole) in comparison to the respective commercial drugs, Azilect (1 mg rasagiline) and Mirapex ER (0.75 mg pramipexole), given alone or in combination. Concentration in plasma (pg/ml) of pramipexole and rasagiline.
Figure 3B:
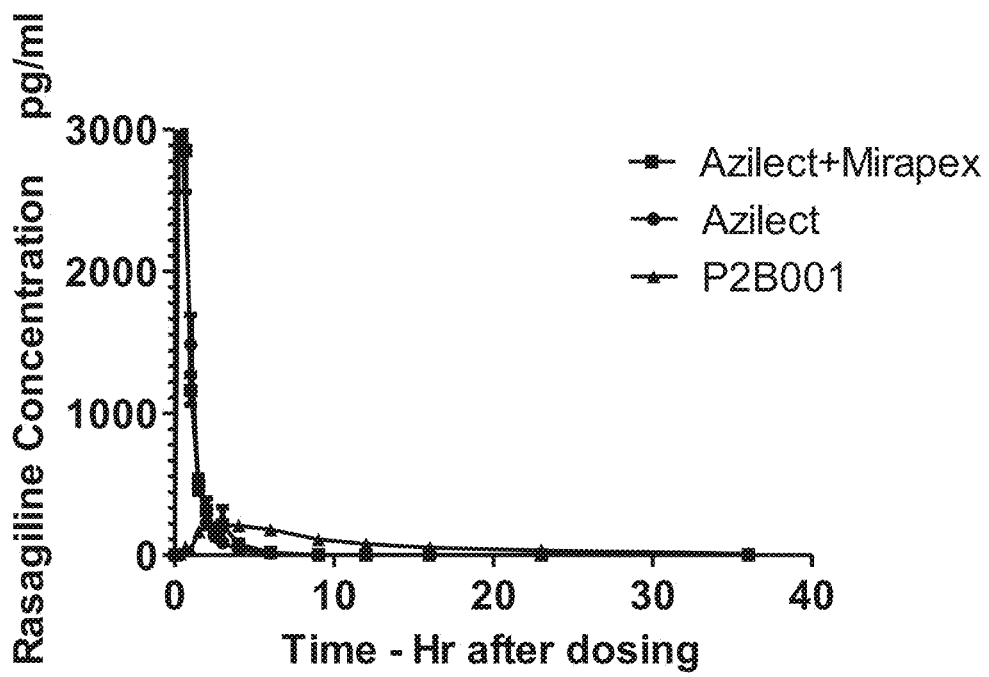

The proprietary extended-release product (FDC) yielded a slightly different (statistically insignificant) pharmacokinetic profile for the pramipexole component than was observed when Mirapex ER was coadministered with Azilect (Cmax was decreased by 15% and $AUC_{inf}$ was increased by 10% (Table 6 and FIGS. 3A-B)).

TABLE 6

Pharmacokinetics of pramipexole and rasagiline

| Treatment | Mean $C_{max}$ (pg/mL) | Mean $AUC_t$ (pg · h/mL) | Mean $AUC_{inf}$ (pg · h/mL) | Mean $T_{max}$ (h) |
|---|---|---|---|---|
| pramipexole | | | | |
| Mirapex ER | 573.8 | 13427.5 | 15889.4 | 11.7 |
| Mirapex ER + Azilect | 550.6 | 12671.1 | 16285.3 | 11.2 |
| Pharma 2B combination product | 469.6 | 10937.7 | 17910.7 | 13.4 |
| rasagiline | | | | |
| Azilect | 4808.1 | 3475.2 | 3533.4 | 0.5 |
| Azilect + Mirapex ER | 4928.5 | 3648.1 | 3678.5 | 0.6 |
| Pharma 2Bcombination product | 275.9 | 2244.9 | 2774.8 | 3.4 |

The pharmacokinetic profile of the rasagiline component of the combination product reflected the differences in formulation (extended release versus immediate release) used in the other study arms. The $C_{max}$ of rasagiline from the combination product was approximately 95% lower while the $AUC_{inf}$ was 22% lower than that of Azilect when coadministered with Mirapex ER.

Taken together, this study shows that co-administration of pramipexole and rasagiline has no effect on the pharmacokinetic profiles of the two drugs and that the combination product formulation delivers pramipexole similar to Mirapex ER. Also, the combination product formulation yields an extended-release of rasagiline without significantly impacting the overall exposure to the drug. Furthermore, these data suggest a promising safety profile of drug combination.

Example 4

Phase IIB Clinical Trial for Evaluation of Applicant's Fixed Dose Combination Product Applicant intends to show that their proprietary combination product has benefits and is well-tolerated with a good safety profile in early Parkinson's disease patients.

This is done by utilizing a dose-ranging study comparing 3 doses of Pharma 2b combination product to placebo in order to study the safety, tolerability and efficacy of this therapy and to identify the best low dose combination that will lead to the highest clinical efficacy concurrently with reduced side effects.

The primary objective is the assessment of efficacy, safety and tolerability of 3 different doses of the combination product and the secondary objective is the assessment of the effect of the combination product on sleep, mood and quality of life (QOL).

Study Plan.

Applicant's study is a phase IIB, randomized, double blind, placebo-controlled, parallel groups, multi-center, dose-ranging study with 3 combination doses. Each component dose is used at a lower dose than is commonly used in the management of patients with early stage Parkinson's disease. The study population includes 200 early stage Parkinson's disease patient volunteers (Parkinson's disease diagnosis consistent with UK Parkinson's Disease Society Brain Bank Clinical Diagnostic Criteria and Modified Hoehn and Yahr staging<3), that are recruited from community and academic hospitals in USA and Israel at a total of 45 sites, among them about 40 sites in USA and 5 in Israel.

Patient volunteers are randomly assigned to one of four treatment groups (50 subjects per group): and receive one of three different doses of the combination product, where the doses of rasagiline will vary between 0.1 mg to 0.75 mg and the dose of pramipexole will vary from 0.1 to 0.6 mg, or a matching placebo.

All treatments are taken orally once a day in the morning before breakfast, at about the same time every day.

The study is divided into 3 phases; screening phase (maximum of 4 weeks), treatment and maintenance phase (12 weeks) and additional safety phase (2 weeks).

The following outcomes are measured: Efficacy in which the primary endpoint is the change from baseline to final visit (week 12) in total Unified Parkinson's Disease Rating Scale (UPDRS) score (defined as sum of parts II—activity of daily life and III-motor evaluation, scores between 0 to 160). Secondary endpoints will include change from baseline to 12 weeks in UPDRS activity of daily life (ADL) and motor sub-scores, Beck Depression Inventory®-II (BDI-II), Parkinson Disease Questionnaire 39 (PDQ39), and Clinical Global Impression (CGI) of subject and investigator. Safety will be assessed by adverse event reporting (frequency and incidence) and scale assessments of sleep, daytime sleepiness, depression, suicidality, impulse control behaviors. Tolerability will be assessed by percentage of subjects that complete the trial on treatment assignment. Over the 12-week trial UPDRS assessments and clinical safety evaluations will be made every 2-4 weeks. The primary analysis of efficacy will compare active dosage groups to placebo using a mixed model repeated measures (MMRM).

Example 5

Phase IIB Clinical Trial for Evaluation of Applicant's Fixed Dose Combination Product at Two Different Doses Pharma Two B conducted a phase 2B clinical trial entitled "A Phase 2B, Twelve-week Multi-Center, Randomized, Double-Blind, Placebo-Controlled, Parallel Group Study, To Determine the Safety, Tolerability and Efficacy of Two Doses of Once Daily FDC in Subjects with Early Parkinson's Disease (PD)".

Objective:

The study intends to show that the Fixed Dose Combination of the present invention as defined below (FDC), has clinical benefits and is well-tolerated with a good safety profile in early Parkinson's disease patients. This was done by utilizing dose-ranging study comparing 2 doses of FDC to placebo in order to study the safety, tolerability and efficacy of this therapy and to identify the best low dose combination that will lead to the highest clinical efficacy concurrently with reduced side effects.

Study Outcomes:

The primary endpoint of this study was the change from baseline to final visit (week 12) in total Unified Parkinson's Disease Rating Scale (UPDRS) score (defined as sum of parts I, II and III), compared to Placebo.

The key secondary endpoints for this study were total UPDRS responder analysis (in which a subject defined as a treatment responder in case that the 12-Weeks/Last Observed Value (LOV) improvement from baseline in the total UPDRS was of 4 points or more), change from baseline to week 12/LOV in total PDQ39, motor UPDRS (UPDRS III), Activities of Daily Living (ADL) UPDRS (part II) scores.

Exploratory endpoints will provide additional insight into the therapeutic effect of the two doses of FDC as compared to placebo. The exploratory endpoints included: Change from baseline to week 12 in UPDRS I+II score, mentation UPDRS (UPDRS I), Clinical Global Impression-Severity CGI-S responder analysis, sub domains of PDQ39 scale. In addition some safety outcomes were evaluated; Parkinson's Disease Sleep Scale (PDSS-2) total and sub domains and Beck Depression Inventory®-II (BDI-II) scores.

Further safety evaluations included the Epworth Sleepiness Scale (ESS), questionnaire for Impulsive-Compulsive Disorders in Parkinson's Disease (QUIP) and Columbia Suicide Severity Rating Scale (C-SSRS).

Study Design:

The study was a randomized, double blind, placebo-controlled, parallel-group, multi-center, dose ranging study and was conducted in 29 sites, 24 in the United States (US) and 5 in Israel.

Subjects:

A total of 149 early PD naïve subjects were randomized in a 1:1:1 ratio to receive FDC-A (pramipexole dihydrochloride 0.6 mg/Rasagiline 0.75 mg) once daily (N=49), FDC-B (pramipexole dihydrochloride 0.3 mg/Rasagiline 0.75 mg) once daily (N=50) or Placebo (N=50). Most of the subjects completed study protocol and only 13 subjects (8.7%) terminated study protocol earlier due to adverse events or withdrawal of consent.

Interventions:

Study medication was taken orally once a day in the morning 2 hours before breakfast, on an empty stomach for a period of 12 weeks+/−3 days.

Study Procedures:

The study included 6 visits. The first visit allowed screening of potential subjects for the study. Eligible subjects were enrolled and randomized at baseline visit. The treatment phase, when subjects received treatment with the investigational drugs or the matching placebo included 3 visits, at 4, 8 and 12 weeks after baseline. During the treatment phase, subjects' condition was evaluated every 4 weeks (visits 2-5). Vitals, adverse events questioning, UPDRS I, II and III, QUIP and C-SSRS questionnaires were performed every visit. PDQ39, ESS, PDSS-2, BDI-II and CGI-S scales were performed only at baseline and week 12/early termination visits. A follow up safety visit was performed two weeks after treatment phase was completed, at week 14. Additional safety assessments, such as Electro Cardiogram (ECG), general laboratory tests and physical examination were done in screening and follow up safety visits.

Results:

The study demonstrates that both dosages FDC-A (pramipexole dihydrochloride 0.6 mg/Rasagiline 0.75 mg) and FDC-B (pramipexole dihydrochloride 0.3 mg/Rasagiline 0.75 mg) induced reductions of 5.97 and 5.14, respectively, in the mean total UPDRS scores from baseline to week 12. The mean of total UPDRS score reduction for placebo treated subjects was only 1.3 as shown in Table 7 and FIG. 4. Treatment effect expressed as mean reduction in total UPDRS score relative to placebo, were −4.66 (p=0.0004), and −3.84, (p=0.0027), for FDC-A and FDC-B, respectively.

Figure 4:
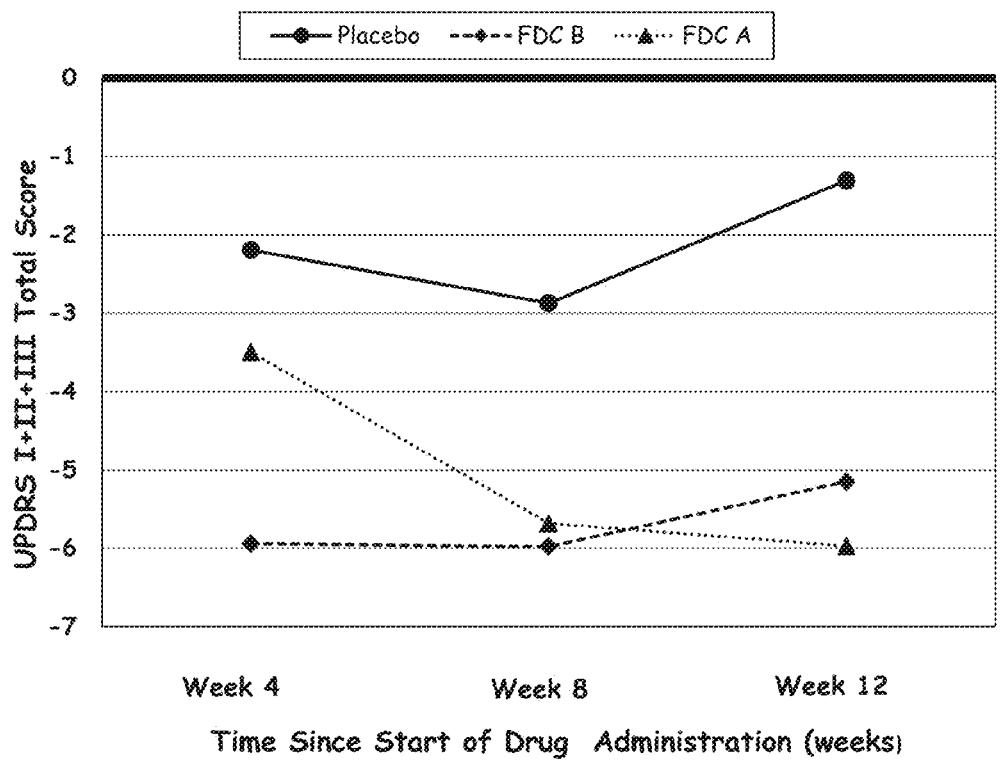
FIG. 4 depicts Intention to Treat (ITT)—Repeated Measures Analysis of Covariance (MMRM) Total UPDRS (I+II+III): Change from Baseline. Model Adjusted Means (+SE) of Change from Baseline. X-axis, time after baseline (weeks); Y-axis, total UPDRS score.

FIG. 4 shows that treatment effect relative to placebo as expressed as mean reduction in total UPDRS score was dose dependent, −4.66(95% CI −7.203 to −2.128) p=0.0004, and −3.84(−6.324 to −1.360), p=0.0027 for FDC-A and FDC-B, respectively.

Figure 5:
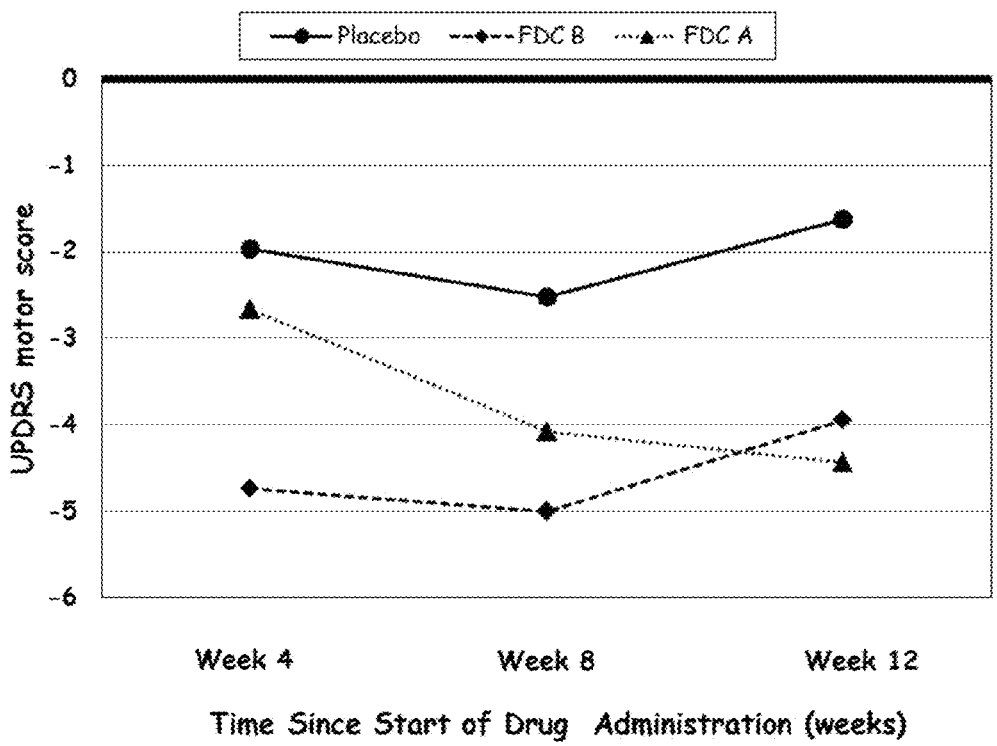
FIG. 5 depicts ITT—Repeated Measures Analysis of Covariance (MMRM). Motor UPDRS (UPDRS III): Change from Baseline. Model Adjusted Means (+SE) of Change from Baseline. X-axis, time since start of drug administration (weeks); Y-axis, UPDRS motor score.

Both motor (UPDRS III) and ADL (UPDRS II) sub-scales showed similar results and contribute together to the overall treatment effect. FIG. 5 shows the change from baseline to week 12 in motor UPDRS scores. Both FDC-A and FDC-B have a significant dose dependent reduction in motor UPDRS subscale score relative to placebo, with p-value of 0.00058 and 0.00191 for FDC-A and FDC-B, respectively.

TABLE 7

Intention To Treat (ITT) Analysis Set: UPDRS - Total UPDRS I + II + III score.

| Treatment Group | Visit | Estimate (LSM) | SE | P-Value | Lower 95% CI Limit | Upper 95% CI Limit |
|---|---|---|---|---|---|---|
| Placebo | Week 4 | −2.1935 | 0.8497 | 0.0110 | −3.8750 | −0.5120 |
|  | Week 8 | −2.8719 | 0.7983 | 0.0005 | −4.4515 | −1.2924 |
|  | Week 12 | −1.3050 | 0.8797 | 0.1406 | −3.0467 | 0.4367 |
| FDC-B | Week 4 | −5.9387 | 0.8570 | <.0001 | −7.6345 | −4.2430 |
|  | Week 8 | −5.9780 | 0.8095 | <.0001 | −7.5794 | −4.3767 |
|  | Week 12 | −5.1475 | 0.9029 | <.0001 | −6.9344 | −3.3606 |
| FDC-A | Week 4 | −3.4966 | 0.8696 | <.0001 | −5.2173 | −1.7760 |
|  | Week 8 | −5.6819 | 0.8391 | <.0001 | −7.3413 | −4.0225 |
|  | Week 12 | −5.9712 | 0.9422 | <.0001 | −7.8357 | −4.1067 |

Mixed model repeated measures (MMRM) Results of Change from Baseline (Adjusted for Pooled Sites and Baseline Measurements) and Least Squares Means (LSM) of Changes from Baseline by Treatment Group and Visit.

The results indicate a statistically significant reduction in total UPDRS scores from baseline to week 12 in both active treatments FDC-A and FDC-B in a dose dependent manner.

In addition to the primary endpoint, Applicant's clinical study shows statistically significant results in all secondary endpoints (Table 8).

Figure 6:
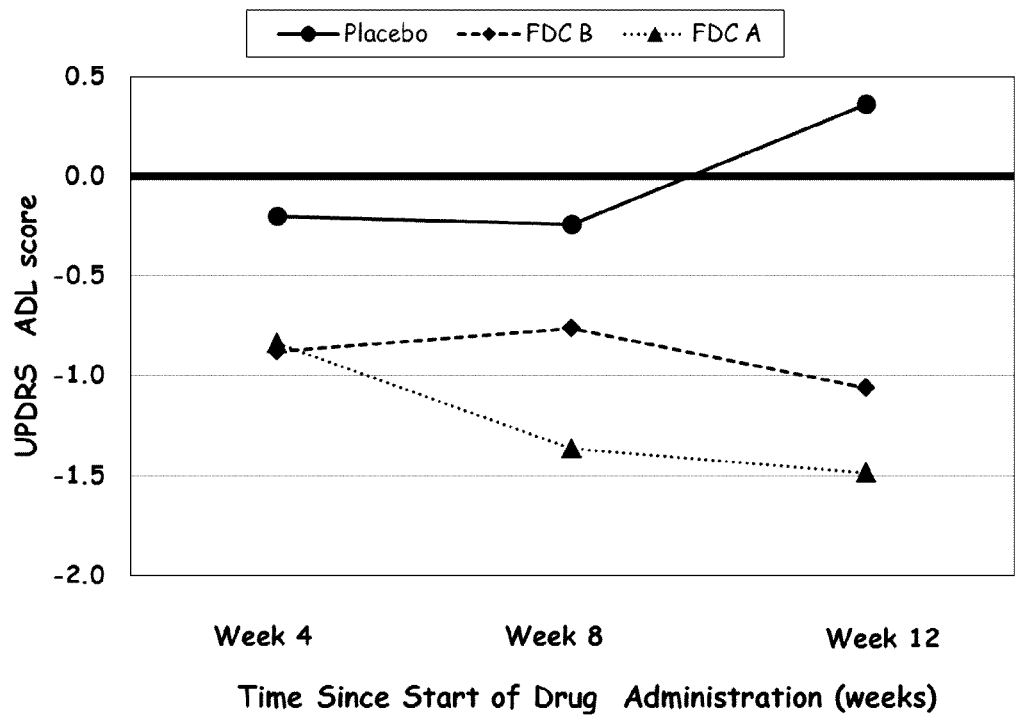
FIG. 6 shows ITT—Repeated Measures Analysis of Covariance (MMRM). ADL UPDRS (UPDRSII): Change from Baseline. Model Adjusted Means (+SE) of Change from Baseline. X-axis, time after baseline (weeks); Y-axis, UPDRS ADL score.
Figure 7:
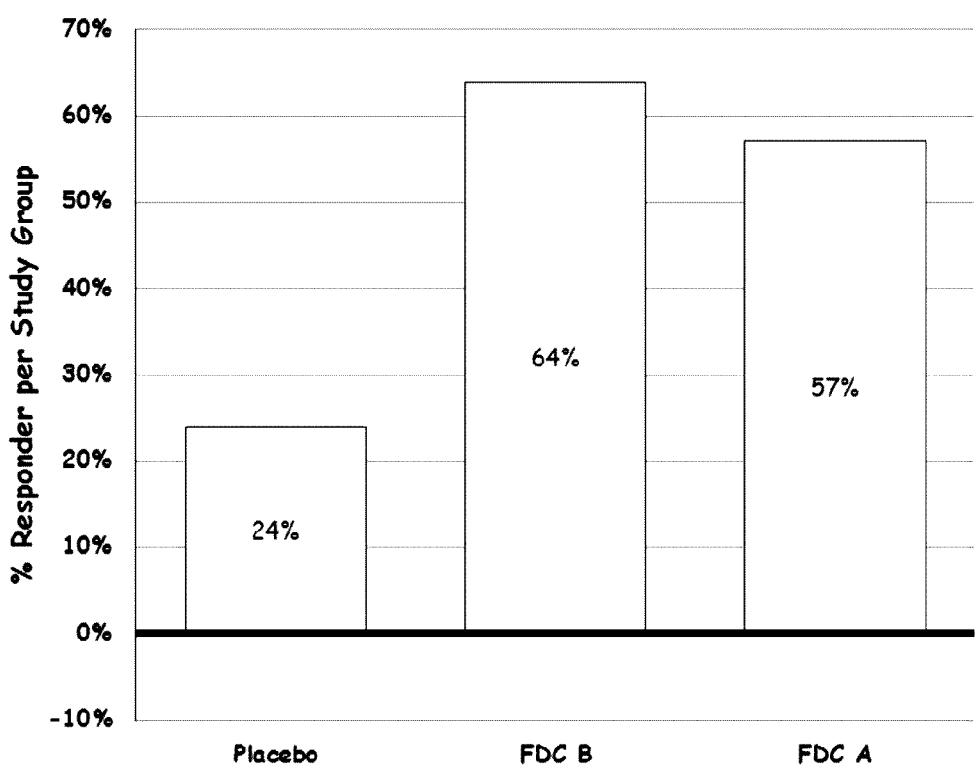
FIG. 7 shows ITT Analysis Set-Total UPDRS (I+II+III), Improvement of at least 4 points UPDRS score.

The contribution of ADL UPDRS (UPDRS III) is shown in FIG. 6. Both FDC-A and FDC-B have a significant dose dependent reduction in ADL UPDRS subscale score relative to placebo, with p-value of 0.0004 and 0.005 for FDC-A and FDC-B, respectively Responder analysis (FIG. 7) demonstrates that 28 subjects out of 49 subjects (57.1%) in the FDC-A group have an improvement of 4 or more points in total UPDRS score, p=0.001 and 32 subjects out of 50 subjects (64%) in FDC-B group have such improvement with p-value of 0.0002.

TABLE 8

Summary of significance testing done for primary and secondary endpoints.

| Contrast Order of Testing | Contrasts to be Tested in the Order Listed |
|---|---|
| 1st p = 0.0004 | Primary Endpoint: Change from baseline to Week 12/Termination visit in the total UPDRS score - FDC-A vs. Placebo Contrast. |
| 2nd p = 0.0027 | Primary Endpoint: Change from baseline to Week 12/Termination visit in the total UPDRS score FDC-B vs. Placebo Contrast. |
| 3rd p = 0.0010 | Secondary Endpoint: Total UPDRS Responders Analysis (4 UPDRS Points) -- FDC-A vs. Placebo Contrast. |
| 4th p = 0.0002 | Secondary Endpoint: Total UPDRS Responders Analysis (4 UPDRS Points) - FDC-B vs. Placebo Contrast. |
| 5th p = 0.0097 | Secondary Endpoint: Change from baseline to Week 12/Termination visit in the Total PDQ39 score -- FDC-A vs. Placebo Contrast. |
| 6th p = 0.0058 | Secondary Endpoint: The change from baseline to Week 12/Termination visit in the motor UPDRS score -- FDC-A vs. Placebo Contrast. |
| 7th p = 0.0004 | Secondary Endpoint: The change from baseline to Week 12/Termination visit in the ADL UPDRS score -- FDC-A vs. Placebo Contrast. |
| 8th p = 0.0509 | Secondary Endpoint: Change from baseline to Week 12/Termination visit in the Total PDQ39 score - FDC-B vs. Placebo Contrast. |
| 9th p = 0.0191 | Secondary Endpoint: The change from baseline to Week 12/Termination visit in the motor UPDRS score - FDC-B vs. Placebo Contrast. |
| 10th p = 0.0050 | Secondary Endpoint: The change from baseline to Week 12/Termination visit in the ADL UPDRS score - FDC-B vs. Placebo Contrast. |

TABLE 9

Frequency and incidence of Treatment Emerged Adverse Events

| | AEs Causality | | | | | | | | |
|---|---|---|---|---|---|---|---|---|---|
| | Placebo | | | FDC-B | | | FDC-A | | |
| | No. Events | No. Subj. | % of Subj. | No. Events | No. Subj. | % of Subj. | No. Events | No. Subj. | % of Subj. |
| All AEs | 60 | 27 | 54 | 68 | 30 | 60 | 86 | 37 | 75.5 |
| Not related | 26 | 14 | 28 | 34 | 18 | 36 | 24 | 14 | 28.6 |
| Related | 34 | 18 | 36 | 34 | 22 | 44 | 62 | 33 | 67.3 |
| % of related AEs from total | 57% | 67% | 67% | 50% | 73% | 73% | 72% | 89% | 89% |

Safety:

Overall, 96% of the subjects in the placebo group, 90% of the subjects in FDC-B group and 87.7% of subjects in FDC-A group, completed the study. The % of patients with Adverse Events (AEs) leading to discontinuation of the study was 4% in the placebo group, 4% in the FDC-B group and 12.3% in the FDC-A group. The frequency and Incidence of AEs are summarized in Table 9. AEs incidence and frequency reported in the FDC-B treatment group were very similar to those reported in the placebo group, while for the FDC-A treatment group, about 40% more AEs were reported relative to Placebo. The same ratio is seen when dividing the AEs to those defined by the Doctor as "related to the study drug" and "not related to study drug". All AEs reported are known as AEs observed for the active ingredients, particularly to Pramipexole. No unexpected AEs were observed.

CONCLUSION

Applicant's clinical trial results demonstrate, for the first time, that combination of low dosages of rasagiline with two pramipexole doses that were previously used only for titration, provide a highly significant positive clinical effect in early stage PD patients, when compared to placebo. Both dosages, FDC-A and FDC-B, in dose dependent manner, were found to be significantly active in improvement the symptoms of PD, in early patients in all assessments done in this study including UPDRS total score and sub scales, PDQ39 and total UPDRS responder analysis. Moreover, both FDC-A and PDC-B are well tolerated and the profile of AEs is favorable, particularly in the FDC-B (pramipexole dihydrochloride 0.3 mg/Rasagiline 0.75 mg) treatment group.

The clinical study results strongly support the observations from the preclinical studies and the scientific hypothesis of the product development, claiming that the strong synergy between rasagiline and pramipexoel, enhanced by the adapted sustained release profile allowing the drugs to act together for a longer time, lead to a high clinical effect of the combination, which was never before shown in the low doses used in FDCs. Moreover, the clinical study results are highly unexpected in light of a previous recent study with the two drugs composing the FDC. Hauser et al. (Randomized, controlled trial of rasagiline as an add-on to dopamine agonists in Parkinson's disease. Mov Disord. 2014 July; 29(8):1028-34) studied the clinical effect of adding 1 mg immediate release rasagiline to patient that were already receiving currently used therapeutic doses of pramipexole, averaging at 1.5 mg pramipexole per day. In this study, the combined effect on total UPDRS score was a reduction of 2.4 UPDRS points compared to placebo. This result is remarkably lower than the reduction induced by FDC-A (4.6 UPDRS points compared to placebo) and FDC-B (3.8 UPDRS points compared to placebo). Thus, the results of the clinical study of FDC, where the doses of both drugs were lower, but the clinical effect was notably higher, are surprising and unexpected, and may be attributed to the fact that in low doses, synergistic effects are more prominent, while in higher doses, the mechanisms could be contradicting rather than complementing each other. The comparison of the clinical study results with the published results of Houser et at indicates again, that the advantages of the FDC cannot be achieved by simply taking the two commercial drugs in their currently available dosage forms.

The invention claimed is:

1. A pharmaceutical composition for use in treatment of Parkinson's disease comprising a pharmaceutically acceptable carrier and a fixed dose combination of pramipexole and rasagiline, wherein the fixed dose combination contains a subtherapeutic dose of pramipexole and a subtherapeutic dose of rasagiline, and the molar ratio of pramipexole to rasagiline is in the range of 1:1.2 to 1:20.

2. The pharmaceutical composition of claim 1, wherein said fixed dose combination contains from 0.05 mg to 0.83 mg of pramipexole and from 0.06 mg to 1.0 mg of rasagiline.

3. The pharmaceutical composition of claim 1, wherein said pramipexole and rasagiline are formulated for extended release.

4. The pharmaceutical composition of claim 2, wherein said pramipexole and rasagiline are formulated for extended release.

5. The pharmaceutical composition of claim 4, wherein said fixed dose combination contains 0.3 mg or 0.6 mg pramipexole and 0.75 mg rasagiline.

6. The pharmaceutical composition of claim 3, in the form of a monolithic matrix; a tablet, disintegrating tablet, dissolving tablet, or chewable tablet; a capsule or sachet; or a depot system based on a biodegradable polymer.

7. The pharmaceutical composition of claim 3, formulated for oral administration.

8. The pharmaceutical composition of claim 4, formulated for oral administration.

9. The pharmaceutical composition of claim 5, formulated for oral administration.

10. The pharmaceutical composition of claim 4 comprising extended-release pellets comprising:
   (i) an inert pellet core;
   (ii) a drug layer coating said pellet core, said drug layer comprising an active agent comprising pramipexole, rasagiline or both, or a pharmaceutically acceptable salt thereof, optionally suitably admixed with a binder and/or a film-former polymer, and further optionally admixed with a glidant;

(iii) optionally an isolating/protecting sub-coating layer coating said drug layer; and (iv) an extended-release coating layer coating said sub-coating layer, if present, or said drug layer.

11. The pharmaceutical composition of claim 10, wherein said sub-coating layer comprises a film-former polymer and optionally a glidant.

12. The pharmaceutical composition of claim 11, wherein said extended-release coating layer comprises:

(i) at least one pH-independent polymer and optionally a pore-forming agent, wherein the extended-release pellet has a pH-independent in vitro release characteristic;

(ii) a pH-independent polymer, a hydrophilic release modulator polymer, and optionally a hydrophobic or hydrophilic plasticizer, and/or a glidant; or (iii) a mixture of a pH-dependent enteric-coating polymer and a pH-independent polymer, wherein the extended-release pellet has a close to zero order in vitro release characteristic at pH value of up to pH 7.4.

13. The pharmaceutical composition of claim 12, wherein:

(i) said pH-independent polymer is ethyl cellulose, Surelease®, Eudragit® RL, Eudragit® RS, Eudragit® NE, or a combination thereof;

(ii) said pH-dependent enteric-coating polymer is Eudragit® S, Eudragit® L 55, Kollicoat®, hydroxypropylmethyl cellulose phthalate (HPMCP), alginates, carboxymethylcellulose, or a combination thereof;

(iii) said pore-forming agent is PVP, PEG, HPMC, HPC, methylcellulose, 1,2-propylene glycol, lactose, sucrose, talc, or a combination thereof;

(iv) said hydrophilic release modulator polymer is HPMC, HPC, PVP, PEG, or a combination thereof; and (v) said plasticizer is dibutyl sebacate; dibutyl phthalate; a citrate ester; propylene glycol; a low molecular weight poly(alkylene oxide); or a combination thereof.

14. The pharmaceutical composition of claim 10, wherein:

(i) said binder is a polyvinyl pyrrolidone (PVP), hydroxypropylmethyl cellulose (HPMC), hydroxypropyl cellulose (HPC), microcrystalline cellulose, or a combination thereof;

(ii) said film-former polymer is PVP, HPMC, HPC, microcrystalline cellulose, or a combination thereof; and (iii) said glidant is talc, colloidal silicon dioxide, glyceryl monostearate, or a combination thereof.

15. The pharmaceutical composition of claim 10, wherein said extended release pellets comprise:

(i) an inert pellet core; a drug layer comprising said active agent admixed with PVP as a film-former polymer/binder and with talc extra fine as a glidant; and an extended-release (ER) coating layer comprising ethylcellulose as a pH-independent polymer, and PEG as a pore-forming agent, wherein the amount of said film-former polymer/binder is up to 90% by weight of the entire drug layer, or from 0.5% to 20% by weight of the entire pellet; the amount of said glidant is up to 30% by weight of the entire drug layer, or from 0.1% to 10% by weight of the entire pellet; the amount of said pH-independent polymer is from 50% to 90% by weight of the entire PE coating layer, or from 10% to 30% by weight of the entire pellet; and the amount of said pore-forming agent is from 1% to 20% by weight of the entire ER coating layer, or from 0.1% to 10% by weight of the entire pellet; or (ii) an inert pellet core; a drug layer comprising said active agent admixed with PVP as a film-former polymer/binder and with talc extra fine as a glidant; an isolating/protecting sub-coating layer comprising PVP as a film-former polymer; and an ER coating layer comprising ethylcellulose as a pH-independent polymer, PEG as a pore-forming agent, and talc extra fine as a glidant, wherein the amount of said film-former polymer/binder in said drug layer is up to 90% by weight of the entire drug layer, or from 0.5% to 20% by weight of the entire pellet; the amount of said glidant in said drug layer is up to 30% by weight of the entire drug layer, or from 0.1% to 10% by weight of the entire pellet; the amount of said film-former polymer in said sub-coating layer is up to 100% by weight of the entire sub-coating layer, or from 0.5% to 20% by weight of the entire pellet; the amount of said pH-independent polymer is from 50% to 90% by weight of the entire ER coating layer, or from 10% to 30% by weight of the entire pellet; the amount of said pore-forming agent is from 1% to 20% by weight of the entire ER coating layer, or from 0.1% to 10% by weight of the entire pellet; and the amount of said glidant in said ER coating layer is from 0.1% to 20% by weight of the entire ER coating layer, or from 0.1% to 10%, by weight of the entire pellet.

16. The pharmaceutical composition of claim 10, wherein said extended-release pellets are blended with one or more suitable excipients and either filled into a capsule or compressed into a tablet, and wherein said capsule or tablet comprises extended-release pellets comprising pramipexole and extended-release pellets comprising rasagiline, or extended-release pellets comprising both pramipexole and rasagiline.

17. The pharmaceutical composition of claim 1, wherein the molar ratio is in the range of 1:1.2 to 1:10.

18. The pharmaceutical composition of claim 1, wherein the molar ratio is in the range of 1:1.2 to 1:5.

19. The pharmaceutical composition of claim 1, wherein the molar ratio is in the range of 1:1.2 to 1:3.

20. The pharmaceutical composition of claim 6, wherein said tablet is a bi- or multi-layered tablet.

21. The pharmaceutical composition of claim 6, wherein said capsule or sachet is filled with granules, grains, beads, or pellets.

22. The pharmaceutical composition of claim 6, wherein said biodegradable polymer is selected from the group consisting of poly(D,L-lactide) (PLA), polyglycolide (PGA), and poly(D,L-lactide-co-glycolide) (PLGA).

23. The pharmaceutical composition of claim 13, wherein said citrate ester is triethylcitrate or triacetin.

24. The pharmaceutical composition of claim 13, wherein said low molecular weight poly(alkylene oxide) is a PEG, poly(propylene glycol) or a poly(ethylene/propylene glycol).

25. A method for preparing an extended release formulation of a fixed dose combination of pramipexole and rasagiline, or a pharmaceutically acceptable salt thereof, said method comprising the steps of:

(i) dissolving an active agent comprising pramipexole, rasagiline or both, optionally suitably admixed with a binder and/or a glidant, in a suitable solvent system to prepare a uniform suspension;

(ii) applying a coat of the suspension obtained in (i) to inert pellets;

(iii) optionally coating the rasagiline loaded pellets, pramipexole-loaded pellets or pellets loaded with both pramipexole and rasagiline, obtained in (ii) with an insulating/protecting sub-coating layer;

(iv) coating the pellets obtained in (ii) or (iii) with an extended-release coating layer which enables an extended release of said pramipexole and rasagiline thereby obtaining said extended release formulation;

(v) optionally blending the coated pellets obtained in (iv) with a suitable excipient; and (vi) filling said extended release formulation into capsules or compressing said extended release formulation into tablets, wherein said capsules or tablets comprise a ratio of pramipexole-loaded pellets and rasagiline-loaded pellets selected from a range of 1:1.2 to 1:20, 1:1.2 to 1:10, 1:1.2 to 1:5, 1:1.2 to 1:3 or 1:1.2 to 1:2; or said capsules or tablets comprise pellets loaded with both pramipexole and rasagiline at a ratio selected from a range of 1:1.2 to 1:20, 1:1.2 to 1:10, 1:1.2 to 1:5, 1:1.2 to 1:3 or 1:1.2 to 1:2, thereby obtaining an extended release formulation of a fixed dose combination of pramipexole and rasagiline.

26. The pharmaceutical composition of claim 25, wherein said inert pellets are inert nonpareil seeds.

27. A pharmaceutical composition for use in treatment of Parkinson's disease comprising a pharmaceutically acceptable carrier and a fixed dose combination of 0.3 mg pramipexole and 0.75 mg rasagiline, wherein said pramipexole and rasagiline are formulated for extended release.

28. The pharmaceutical composition of claim 27, formulated for oral administration.

29. A pharmaceutical composition for use in treatment of Parkinson's disease comprising a pharmaceutically acceptable carrier and a fixed dose combination of 0.6 mg pramipexole and 0.75 mg rasagiline, wherein said pramipexole and rasagiline are formulated for extended release.

30. The pharmaceutical composition of claim 29, formulated for oral administration.

* * * * *